United States Patent [19]
Walker et al.

[11] Patent Number: 5,728,070
[45] Date of Patent: Mar. 17, 1998

[54] PORTABLE CHEMOTHERAPY TREATMENT DISPENSER SYSTEM

[76] Inventors: Herbert B. Walker, deceased, late of Greensboro, N.C.; by Margaret K. Walker, executrix, 4302 Stonehenge Rd., Greensboro, N.C. 27406

[21] Appl. No.: 382,865

[22] Filed: Feb. 3, 1995

[51] Int. Cl.[6] .................................................. A61M 5/32
[52] U.S. Cl. ................ 604/179; 604/174; 128/DIG. 26
[58] Field of Search .................... 128/DIG. 26; 604/174, 604/179, 180

[56] References Cited

U.S. PATENT DOCUMENTS

| | | | |
|---|---|---|---|
| 1,238,872 | 2/1917 | Bell . | |
| 1,317,659 | 5/1919 | Charles . | |
| 1,696,763 | 12/1928 | Hare | 604/179 |
| 3,895,629 | 7/1975 | Snyder | 128/348 |
| 4,326,517 | 4/1982 | Whitney et al. | 604/179 X |
| 4,416,664 | 11/1983 | Womack | 604/179 X |
| 4,438,763 | 3/1984 | Zablen | 604/179 X |
| 4,666,432 | 5/1987 | McNeish et al. | 604/174 |
| 4,955,867 | 9/1990 | Endo | 604/179 |
| 5,048,512 | 9/1991 | Turner et al. | 128/876 |
| 5,193,553 | 3/1993 | Kalinoski | 128/767 |
| 5,257,987 | 11/1993 | Athayde et al. | 604/892.1 |
| 5,304,145 | 4/1994 | Blair | 604/179 |
| 5,336,195 | 8/1994 | Daneshvar | 128/DIG. 26 X |

FOREIGN PATENT DOCUMENTS

WO 82/04399  12/1982  WIPO ................................ 604/174

*Primary Examiner*—Sam Rimell
*Attorney, Agent, or Firm*—Rhodes, Coats & Bennett, L.L.P.

[57] ABSTRACT

The present invention is directed to a harness system for supporting on a wearer, a portable chemotherapy treatment dispenser. The harness system includes a harness arranged and configured to removably surround a portion of the wearer. A container support means is mounted on the harness at a first location and is adapted to receive and hold a container of chemotherapy medication. A pump holding means is mounted on the harness at a second location and is adapted to receive and hold a pump. The harness may comprise a belt arranged and configured to be worn approximately about the wearer's waist. A shoulder strap may also be provided as part of the harness. The belt portion of the harness may be a brace, such as a back brace.

6 Claims, 3 Drawing Sheets

PORTABLE CHEMOTHERAPY TREATMENT DISPENSER SYSTEM

FIELD OF THE INVENTION

The present invention relates to chemotherapy treatment, and, more particularly, to a harness system for supporting a portable chemotherapy treatment dispenser.

BACKGROUND OF THE INVENTION

Methods and apparatus have recently been developed which allow chemotherapy treatment to be administered away from treatment facilities such as hospitals. These apparatus, commonly referred to as portable chemotherapy treatment dispensers, generally comprise a bag or pouch of chemotherapy medication, a pump, a catheter, and associated tubing. The components of the dispenser are sized so as to be carried by the chemotherapy patient. Typically, the pump is about 4 inches×6 inches×1 inch and weighs about 16 ounces. The bag is typically about 3 inches×7 inches×¾ inch and weighs about 12 ounces when full. Medication is drawn by a pump from the bag through tubing therebetween and forced through tubing between the pump and the catheter. The catheter is suitably inserted into the patient's body, generally in the torso, so that medication dispensed by the pump is administered to the patient.

Heretofore, the components listed above have been provided to patients with a waist bag or "fanny pack." Waist bags of this type generally consist of a belt member with a zippered pouch formed integrally with the belt member. The patient simply puts the pump, the pouch of medication, and the tubing therebetween in the pouch with the tubing to the catheter extending out of the opening in the pouch. This set-up suffers from several drawbacks. First, the waist bag is difficult to conceal. As such, it is highly noticeable when worn with non-casual attire, for example, coat and tie or a dress. Second, the waist bag does not optimally situate and retain the components, and, as a result, they impede movement and become a localized burden. Moreover, the waist bag only loosely affixes the treatment components to the patient's body, thereby allowing the pouch and its contents to swing about during vigorous movement. Such swinging not only impedes the movement of the wearer, but also jostles the components, risking damage to the same.

Thus, there exists a need for a convenient and effective means for holding various components of a portable chemotherapy treatment dispenser. There exists a need for such a means which comfortably and securely distributes the components of the dispenser so as to minimize impediment to the movement of the wearer. Moreover, there exists a need for such a means which serves to conceal the components of the dispenser.

SUMMARY OF THE INVENTION

The present invention is directed to a harness system for supporting apparatus associated with portable chemotherapy treatment. The apparatus generally includes a container of chemotherapy medication, a pump, first tubing interconnecting the container and the pump, and second tubing interconnecting the pump and a catheter. The harness system includes a harness arranged and configured to removably surround a portion of the wearer. Container support means are mounted on the harness at a first location. The container support means is adapted to receive and hold the container of chemotherapy medication. The harness system is further provided with pump holding means mounted on the harness at a second location. The pump holding means is adapted to receive and hold the pump.

Preferably, the harness includes a belt arranged and configured to be worn approximately about the wearer's waist. The harness may also include a shoulder strap. If a shoulder strap is provided, the container support means is preferably mounted on the strap while the pump holding means depends from the belt.

The belt forming a part of the harness may be a brace. If the belt is a brace, preferably, the pump holding means depends from the brace and the container support means is mounted on the brace. Moreover, the container support means is preferably secured to the interior surface of the brace.

An object of the present invention is to provide a convenient and effective harness system for holding the various components of a portable chemotherapy treatment dispenser.

An object of the present invention is to provide such a harness system for comfortably and securely distributing the components of the dispenser so as to minimize impediment to the movement of the wearer.

An object of the present invention is to provide such a harness system which is cost effective to manufacture.

An object of the present invention is to provide a harness system as described above which may be easily put on and removed.

An object of the present invention is to provide a harness system as described above which is easily concealed and which serves to conceal the components of the dispenser.

DETAILED DESCRIPTION OF THE PREFERRED EMBODIMENT

Figure 1:
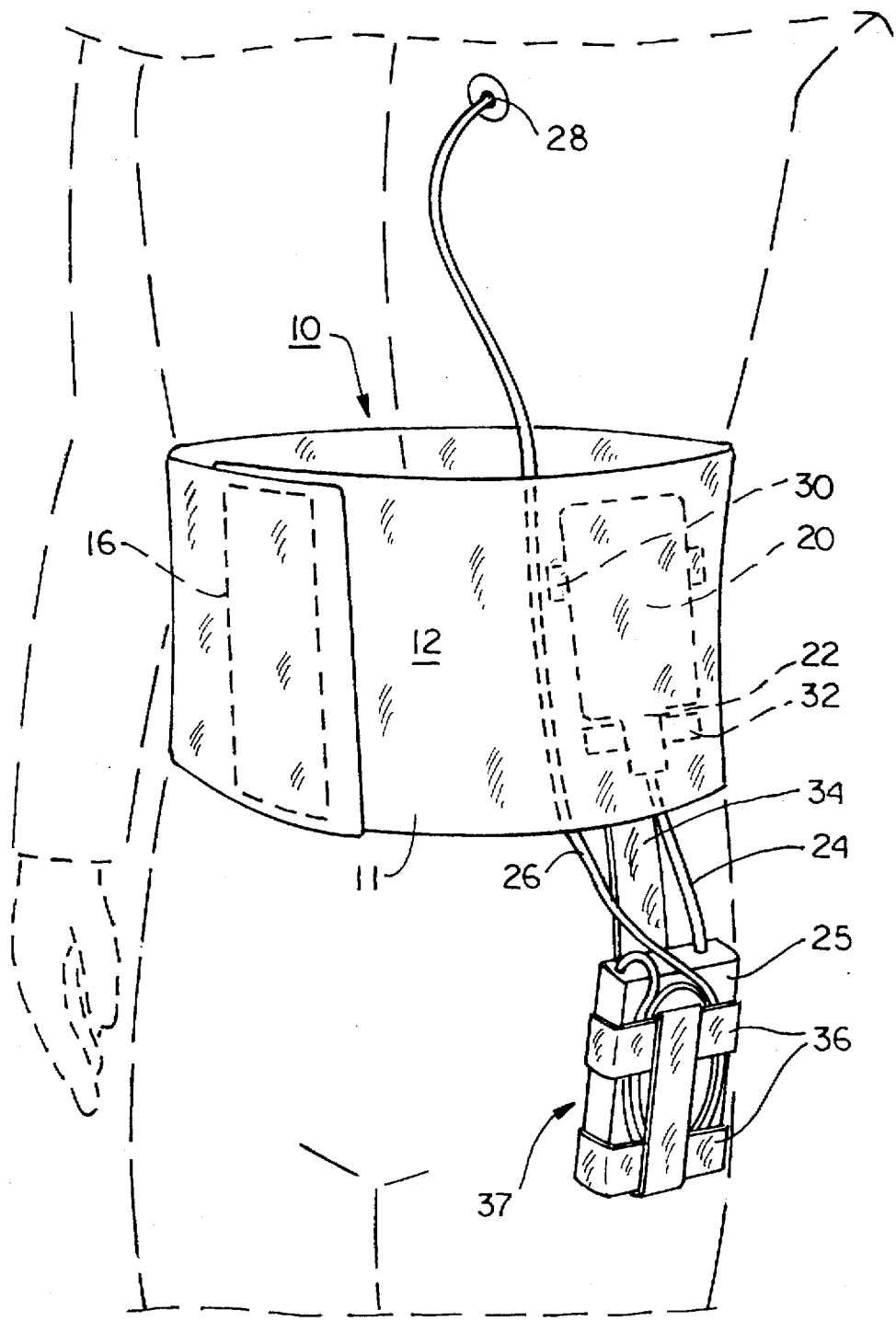
FIG. 1 is a perspective view of a first embodiment of the harness system of the present invention, the harness system being worn by a patient and the chemotherapy treatment dispenser components being mounted therein.
Figure 2:
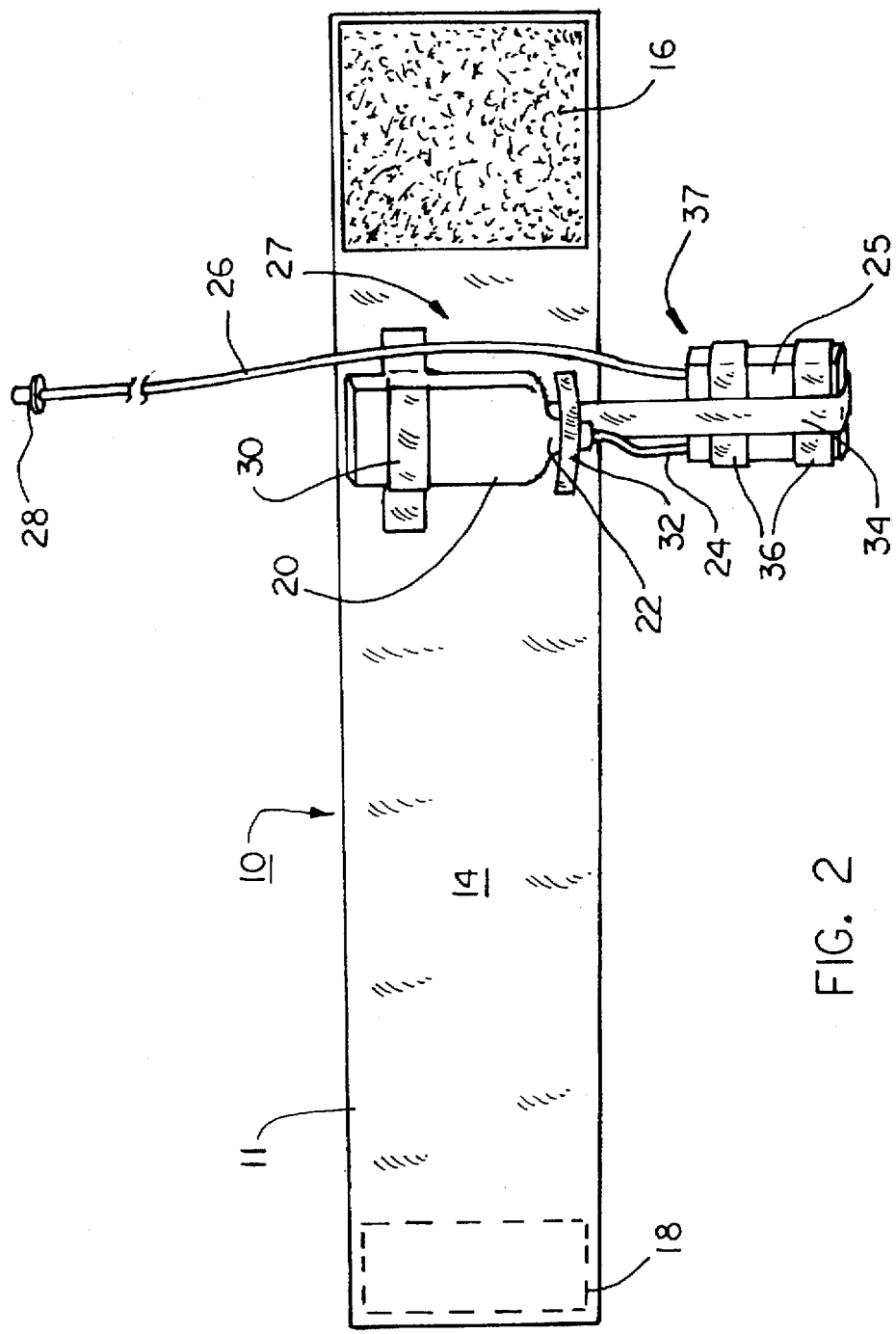
FIG. 2 is a front plan view of the harness system according to the first embodiment of the present invention showing the interior surface of the harness system.

With reference to FIGS. 1 and 2, a harness system 10 according to a first embodiment for supporting a portable chemotherapy treatment dispenser is shown therein. The portable chemotherapy treatment dispenser includes a container or pouch 20 of chemotherapy medication, a pump 25, a catheter 28, first tubing 24 interconnecting pump 25 and pouch 20, and second tubing 26 interconnecting pump 25 and catheter 28.

Pouch 20 and pump 25 are conventional as discussed above in the Background of the Invention. Pouch 20 is preferably pliable and includes a rigid neck 22.

Harness system 10 includes a belt or brace 11 having an interior surface 14 and an exterior surface 12. Preferably, brace 11 is formed from a suitable durable, elasticized fabric, as may be found in conventional back braces and kidney belts. Complementary VELCRO™ patches 16 and 18 are provided on the interior and exterior surfaces of brace 11, respectively, for adjustably securing brace 11 about the mid-section of the wearer.

Container support means 27 includes straps 30, 32. The ends of strap 30 are secured to interior surface 14 of brace 11 by stitching, VELCRO™, snaps, or the like. Strap 30 is adapted to receive pouch 20 and, in combination with the interior surface of the brace, hold the pouch securely. Note that strap 30 may be replaced with other suitable holding means, such as a pocket or a releasable cover. Strap 32 is also secured to the interior surface of brace 11. Strap 32 is adapted to receive and securely hold neck 22 of pouch 20. Preferably, strap 32 is secured to the interior surface of the brace by VELCRO™ or the like so that neck 22 may be mounted beneath strap 32 without requiring removal of first tubing 24 from pump 25 or pouch 20.

Pump holding means 37 includes straps 34,36. Depending strap 34 is preferably secured to the interior surface of brace 11. Preferably, strap 34 is releasably secured such that it may be vertically adjusted with respect to brace 11. Secured to a lower portion of strap 34 are straps 36 adapted to receive, surround, and securely hold pump 25.

Methods and materials for fabrication of the above-described harness system will be readily apparent to those of ordinary skill in the art. For example, elasticized fabric joined with stitching may be used.

To use the above-described harness system, the user inserts pump 25 into straps 36. Neck 22 and pouch 20 are placed and secured beneath straps 32 and 30, respectively. As shown in FIG. 1, brace 11 is wrapped around the mid-section of the user and comfortably secured thereabout by engaging VELCRO™ patches 16, 18. The position of pump 25 with respect to the wearer's mid-section may be adjusted by removing and selectively replacing depending strap 34. Catheter 28 is engaged with the body of the wearer. Tubing 26, which may be on the order of six to eight feet long, may be tucked under straps 36, as shown.

It will be appreciated that when the brace and dispenser components are so mounted and covered by regular clothing, pouch 20 will be more or less concealed by brace 11. Also, pump 25 can be selectively positioned in the trousers of the wearer. The various components of the chemotherapy treatment dispenser will be advantageously secured to the wearer so as to firmly hold the dispenser and reduce or eliminate any inhibition the dispenser may cause to the wearer's movement.

Figure 3:
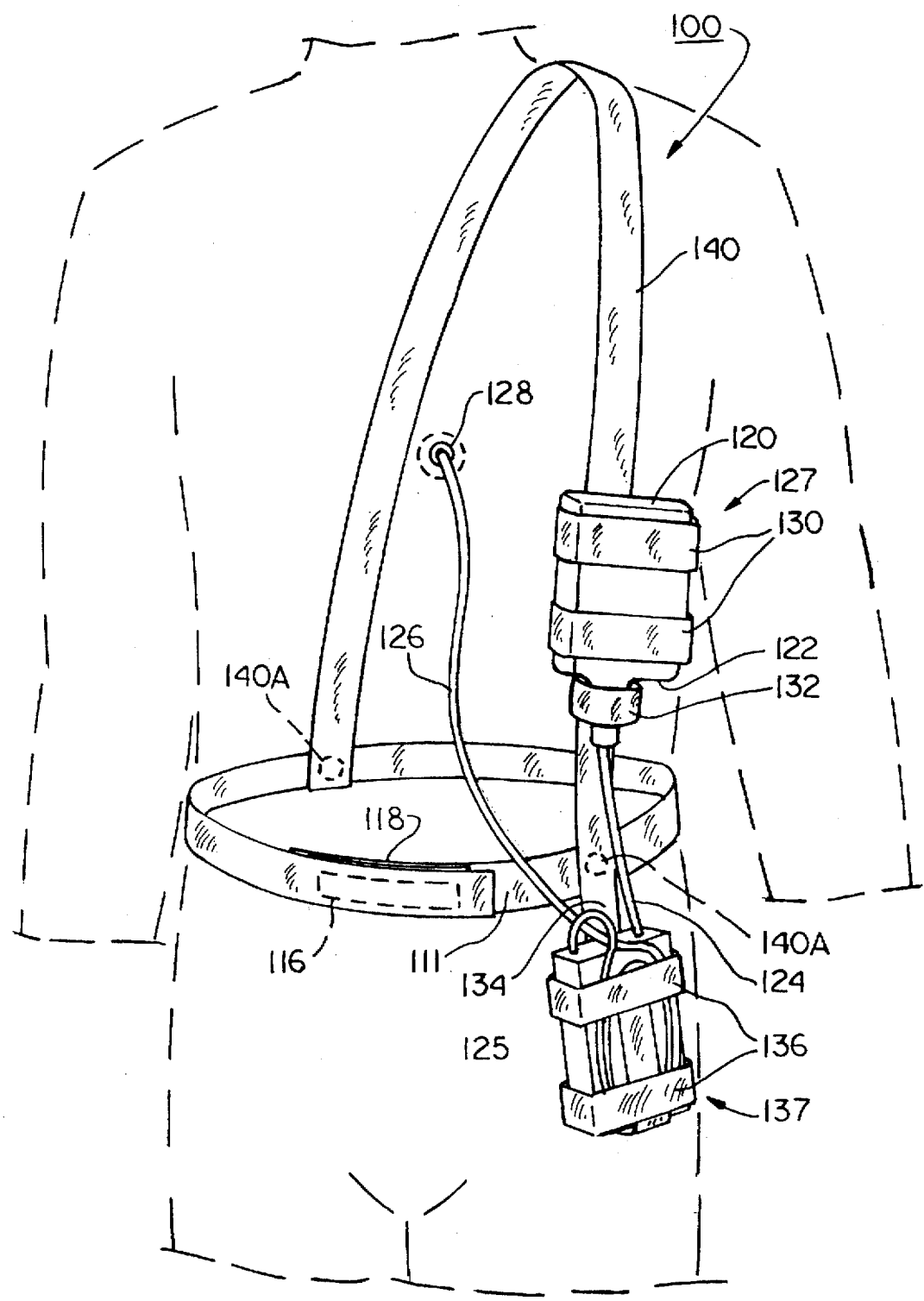
FIG. 3 is a perspective view of a harness system according to a second embodiment of the present invention, the harness system being worn by a patient and the chemotherapy treatment dispenser being mounted therein.

With reference to FIG. 3, a harness system 100 according to a second embodiment of the present invention is shown therein. Harness system 100 includes belt 111 and shoulder strap 140. Ends 140A of shoulder strap 140 are secured to belt 111 by stitching, VELCRO™, or the like. Patches 116, 118 are provided on the interior and exterior surfaces of belt 111, respectively, for adjustably securing belt 111 about the mid-section of the wearer. First tubing 124 extends between pouch 120 and pump 125, one end secured to neck 122 of pouch 120. Second tubing 126 extends between pump 125 and catheter 128.

Container support means 127 includes straps 130, 132. Straps 130 are secured to shoulder strap 140 and are adapted to receive and hold pouch 120. Strap 132, also secured to shoulder strap 140, is adapted to receive and hold neck 122. Preferably, strap 132 is secured to strap 140 by VELCRO™ or the like so that neck 122 may be inserted therein without requiring the removal of first tubing 124 from pouch 120 or pump 125.

Pump holding means 137 includes straps 134, 136. Depending strap 134 is preferably releasably secured to belt 111 and/or shoulder strap 140 by VELCRO™ or the like. Straps 136 are secured to depending strap 134 and are adapted to receive and hold pump 125.

The methods and materials for fabrication of harness system 100 according to the second embodiment will be readily apparent to one of ordinary skill in the art. For example, elasticized fabric joined by stitching may be used.

In use, the wearer secures belt 111 about his or her mid-section by mating VELCRO™ patches 116, 118. Shoulder strap 140 is placed over the shoulder as shown in FIG. 3. Pouch 120 is placed under straps 130 and neck 122 is placed under strap 132. Pump 125 is secured in straps 136. The proximity of the pump to the waist of the wearer may be adjusted by removing and repositioning depending strap 134. Tubing 126 may be tucked under straps 136, as shown.

It will be readily apparent that certain modifications and alterations to the above-described embodiments may be made without departing from the scope of the invention. For example, the container support means and/or the pump holding means may be incorporated into an undershirt or the like in addition to or instead of the aforedescribed brace and strap. All such modifications and alterations are intended to be included within the scope of the claims which follow.

What is claimed:

1. A harness system for supporting a portable chemotherapy treatment dispenser on the wearer, the dispenser being of the type including a container of chemotherapy medication, a medication pump, first tubing interconnecting the container and the pump, and second tubing interconnecting the pump and a catheter, said harness system comprising:

a. a harness arranged and configured to removably surround a portion of the wearer, said harness comprising a belt arranged and configured to be worn approximately about the wearer's waist and a shoulder strap, said shoulder strap having at least two ends, each of said ends secured to said belt, and wherein said strap is arranged and configured to be worn over the wearer's shoulder;

b. container support means mounted on said harness at a first location and adapted to receive and hold the container of chemotherapy medication;

c. pump holding means mounted on said harness at a second location and adapted to receive and hold the pump; and d. wherein said pump holding means depends from said belt and wherein said container support means is mounted on said strap.

2. The harness system of claim 1 wherein said container support means includes an opening formed on a lower portion thereof adapted to receive the first tubing or a neck forming a part of the container.

3. The harness system of claim 1 wherein said pump holding means is adjustably mounted on said belt so that the pump may be selectively positioned with respect to the wearer.

4. A portable chemotherapy treatment system for administering a chemotherapy medication to a patient, comprising:

a. a container for holding the chemotherapy medication;

b. a pump for dispensing the chemotherapy medication, said pump and said container interconnected for fluid communication by a first tubing;

c. a catheter adapted to introduce the chemotherapy medication to the patient's body, said catheter and said pump interconnected for fluid connection by a second tubing;

d. a harness arranged and configured to removably surround a portion of the patient, said harness comprising a belt arranged and configured to be worn approximately about the patient's waist and a shoulder strap, said shoulder strap having at least two ends, each of said ends secured to said belt, and wherein said strap is arranged and configured to be worn over the wearer's shoulder;

e. container support means mounted on said harness at a first location and adapted to receive and hold said container;

f. pump holding means mounted on said harness at a second location and adapted to receive and hold said pump;

g. wherein said pump holding means depends from said belt and wherein said container support means is mounted on said strap; and h. wherein said pump holding means is adjustably mounted on said belt so that said pump may be selectively positioned with respect to the wearer.

5. A portable chemotherapy treatment system for administering a chemotherapy medication to a patient, comprising:

a. a container for holding the chemotherapy medication;

b. a pump for dispensing the chemotherapy medication, said pump and said container interconnected for fluid communication by a first tubing;

c. a catheter adapted to introduce the chemotherapy medication to the patient's body, said catheter and said pump interconnected for fluid connection by a second tubing;

d. a harness arranged and configured to removably surround a portion of the patient, said harness comprising a brace arranged and configured to be worn approximately about the patient's waist;

e. container support means mounted on said harness at a first location and adapted to receive and hold said container;

f. pump holding means mounted on said harness at a second location and adapted to receive and hold said pump; and g. wherein said pump holding means depends from said brace and said container support means is mounted on said brace, said pump holding means adjustably mounted on said brace so that said pump may be selectively positioned with respect to the wearer.

6. A portable chemotherapy treatment system for administering a chemotherapy medication to a patient, comprising:

a. a container for holding the chemotherapy medication;

b. a pump for dispensing the chemotherapy medication, said pump and said container interconnected for fluid communication by a first tubing;

c. a catheter adapted to introduce the chemotherapy medication to the patient's body, said catheter and said pump interconnected for fluid connection by a second tubing;

d. a harness arranged and configured to removably surround a portion of the patient, said harness comprising a belt arranged and configured to be worn approximately about the patient's waist;

e. container support means mounted on said harness at a first location and adapted to receive and hold said container;

f. pump holding means mounted on said harness at a second location and adapted to receive and hold said pump; and g. wherein said pump holding means depends from said belt, said pump holding means adjustably mounted on said belt so that said pump may be selectively positioned with respect to the wearer.

* * * * *